United States Patent [19]

Ledóchowski et al.

[11] 4,139,531
[45] Feb. 13, 1979

[54] 1-NITRO-9-ALKYLAMINOALKYLAMINOA-CRIDINES AND SALTS THEREOF

[75] Inventors: Andrzej Ledóchowski, Gdańsk-Oliwa; Jerzy Gieldanowski; Czeslaw Radzikowski, both of Wroclaw; Barbara Horowska, Gdańsk-Wrzeszcz; Cecylia Kwasniewska-Rokicinska, Gliwice; Barbara Wysocka-Skrzela, Gdańsk; Lucyna Sawinska, Warsaw; Mieczyslaw Medon, Jelenia Góra, all of Poland

[73] Assignee: Politechnika Gdanska, Gdansk-Wrzesoz, Poland

[21] Appl. No.: 771,416

[22] Filed: Feb. 23, 1977

[30] Foreign Application Priority Data

Feb. 25, 1976 [PL] Poland ................................. 187520

[51] Int. Cl.² .................... C07D 219/12; A61K 31/47
[52] U.S. Cl. ..................................... 546/106; 424/257
[58] Field of Search ..................................... 260/279 A

[56] References Cited
U.S. PATENT DOCUMENTS 1,962,277  6/1934  Jensch et al. ..................... 260/279A

FOREIGN PATENT DOCUMENTS 1093847  12/1967  United Kingdom.

OTHER PUBLICATIONS

Konopa et al., Chem. Abstracts, v. 71, 37,302s (1969).
Ledochowski, Chem. Abstracts, v. 67, 64,226u (1967).

*Primary Examiner*—Donald G. Daus
*Assistant Examiner*—Diana G. Rivers
*Attorney, Agent, or Firm*—Haseltine, Lake & Waters

[57] ABSTRACT

1-Nitro-9-alkylaminoalkylaminoacridins and their salts, as well as a method for obtaining these compounds, is described. The 1-nitro-9-alkylaminoalkylaminoacridines have the formula 1,

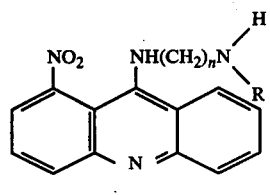

wherein R is methyl, ethyl, propyl, isopropyl, butyl, isobutyl, isopentyl, benzyl or cyclohexyl, whereas n is equal to 2 or 3. The salts are those derived from mineral acids or organic acids. These compounds have anti-neoplastic activity.

1 Claim, 2 Drawing Figures

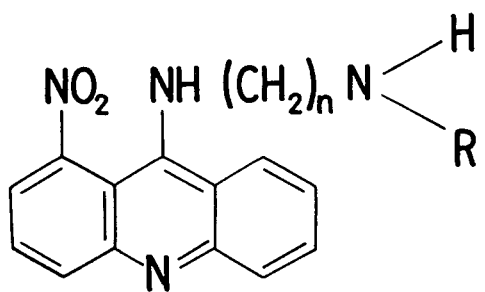
1
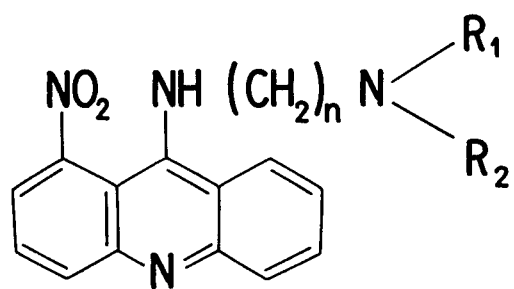
2

1-NITRO-9-ALKYLAMINOALKYLAMINOACRIDINES AND SALTS THEREOF

The present invention relates to 1-nitro-9-alkylaminoalkylaminoacridines, their salts, of the formula 1

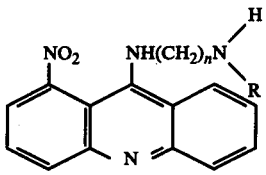

wherein R is methyl, ethyl, propyl, isopropyl, butyl, isobutyl, isopentyl, benzyl, or cyclohexyl, and n is equal to 2 or 3, as well as to a method for their preparation.

Till now there were known, from the British Patent Application No. 1093847, 1-nitro-9-dialkylaminoalkylaminoacridines of the formula 2

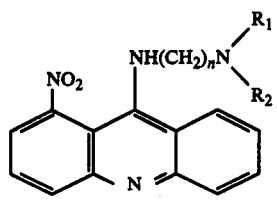

wherein n = 2 or 3, and $R_1 = R_2$ and is a methyl or ethyl group.

These compounds are characterized by having identical substituents at $N^\omega$.

The method for obtaining these compounds is based on a condensation of 1-nitro-9-chloroacridine, melting point 150° to 151° C., with dialkylaminoalkylamine in an organic solvent, e.g., phenol or cresol at a temperature of 20° to 100° C., and, subsequently, on the isolation of the product obtained from the reaction medium using known methods, e.g., through extraction.

A real disadvantage of the compounds described in the prior art is their instability, especially in aqueous solutions, in which they hydrolyze to 1-nitroacridone, a water-insoluble product, which makes their storage impossible for long periods of time.

Moreover, these compounds show photosensitivity, i.e., they are deactivated by light.

The 1-nitro-9-alkylaminoalkylaminoacridines, and their salts, are characterized by the general formula 1 above, wherein R is methyl, ethyl, propyl, isopropyl, butyl, isobutyl, isopentyl, benzyl or cyclohexyl, wherein n is equal to 2 or 3. A method for obtaining the 1-nitro-9-alkylaminoalkylaminoacridines, or their salts, of the formula 1, above, wherein R and n have the meaning given above, according to the present invention, comprises mixing (1-nitroacridyl-9-)-pyridinium chloride or 1-nitro-9-chloroacridine, or their salts, with phenol and heating to a temperature of from 50° to 80° C.; then cooled to room temperature, and alkylaminoalkylamine or its salt is added; the whole reaction mixture is heated again to a temperature of from 50° to 120° C., and subsequently, the reaction mixture is added to a large amount of a non-polar organic solvent, which is immiscible with water; the formed precipitate of monohydrochloride of 1-nitro-9-alkylaminoalkylaminoacridine is made alkaline with a solution of alkaline hydroxide, then is extracted with an organic water-immiscible solvent, is crystallized and dried, and eventually, is converted into salts of mineral acids, as hydrochlorides, hydrobromides, sulphates, or their salts of organic acids, such as lactates, citrates, and succinates; or the formed precipitate of monohydrochloride of 1-nitro-9-alkylaminoacridine is eventually acidified with an ether solution of hydrogen chloride and is then crystallized from the organic solvent.

The second method for the preparation of the 1-nitro-9-alkylaminoalkylaminoacridines or their salts of the formula 1, above, wherein R and n have the meaning given above, is based thereon, that 1-nitro-9-phenoxyacridine, or its salt, is mixed with phenol and alkylaminoalkylamine or its salt is then added, and the reaction mixture is then heated to a temperature of from 50° to 120° C.; the reaction mixture is subsequently poured in to a large amount of an organic, water-immiscible solvent, and the formed precipitate of the monohydrochloride of 1-nitro-9-alkylaminoalkylaminoacridine is made alkaline with a solution of alkaline hydroxide, extracted with an organic water-immiscible solvent, dried and crystallized, and, optionally, converted into salts of mineral acids, e.g., hydrochlorides, hydrobromides, sulphates, or in their salts of organic acids, e.g., lactates, citrates, succinates, or the formed precipitate of monohydrochloride of 1-nitro-9-alkylaminoalkylaminoacridine is, optionally, acidified with an ether solution of hydrogen chloride and crystallized from an organic solvent.

The anti-neoplastic properties of the objective group of new derivatives of 1-nitro-9-aminoacridine, namely, 1-nitro-9-alkylaminoalkylaminoacridines, have been investigated many times using the tests described below and in all these tests a high antineoplastic activity was observed.

I. In vitro methods (1) Tissue culture (KB-lines)

Investigations were carried out using the method of tissue culture elaborated by Eagle and Foley [Cancer Research, 18, 1017(1958)], modified by Smith and collaborators [Cancer Research, 19, 843–847(1959)].

The experiments were carried out on neoplastic cells of human origin, the so-called KB-lines, using Eagle's nutrient medium with 10% addition of calf's serum.

The tests were performed in test-tubes, inoculating them with four milliliters of a suspension (40 to 80 thousand cells), which is tantamount to 40–84 μg of cytoproteins.

The growth of the culture was determined with an increment of the cytoprotein. The determination was carried out photometrically using the Folin-Cicaltean's reagent and applying the method elaborated by Oyama [Proc. Soc. Exp. Biol. Med., 91, 305(1956)].

Simultaneously with the inoculation of the test-tubes with cells, was added 0.2 ml of aqueous solution of the compound tested so that the concentration could have been attained: 100, 10, 1, 0.1, 0.01 and 0.001 μg/ml of the nutrient medium. The test-tubes were incubated at a temperature of 37° C. After 72 hours the increment of the cytoprotein in the test-tubes, in those the preparation was added and in the control ones, was determined.

Each concentration was investigated in parallel by means of two tests. The concentration at which 50% cell protein inhibition was observed as compared to the control was also determined, i.e., by the so-called $ID_{50}$.

$$\% \text{ of inhibition} = 100 \frac{\text{final protein concentration in the control}}{\text{final protein concentration in the control} - \text{final protein concentration in the test} \atop - \text{initial protein concentration in the control}}$$

According to the generally accepted norms, [Leiter et al, Cancer Research, 25, (3/2), 522(1965)], those compounds which are considered to be active, are those in which $ID_{50} \leq 1$ μg/ml. Leiter and collaborators (ibid) think that such compounds, without regard to the results obtained by in vivo experiments, should be subjected to clinical examinations.

The compounds of the group mentioned above, were tested using this method many times. The value $ID_{50}$ amounts to from 0.01 to 0.001 μg/ml, respectively.

(2) The Miyamura method (Cells of Ehrlich's cancer)

The method is based on determining the inhibition of dehydrogenase activity of cells of Ehrlich's cancer ($5.10^6$ in ml) by the compounds investigated, the measure of which is the diameter of the zone of non-reduced redox-indicator (redox-pigment) (resazurine), which forms around a cylinder containing a 1% solution of the compound being tested after five hours of incubation at a temperature of 37° C.

According to generally accepted criteria, the compounds for which the inhibition zone is at least 20 mm, are considered as active ones.

The derivatives of acridine, presented here, show an extraordinarily high anti-neoplastic activity in this test, which amounts to from 26 to 42 mm for individual compounds.

(3) Inhibition of the germination of cress seeds (growth test)

On a Petri dish with a diameter of 80 mm are placed, in a uniform manner if possible, 20 to 25 cress seeds on two layers of filter paper. Subsequently, 30 ml of solution of the compound to be tested at a concentration 1 mg/ml is poured into each of these Petri dishes, whereas, distilled water is added to the control samples. The dishes are incubated for 24 hours at a temperature of 20°–30° C., and the length of germs formed is measured.

The inhibition effect is expressed by percent of the decrease in the mean length of the germs tested, when compared to the control sample.

The percent value of inhibition of the cress seeds germination is 86 to 88% for the group of compounds of the present invention.

II. The in vivo methods

The growth inhibition of the Crocker mice sarcoma (Sa-180).

For this investigation, mice of about three months in age and a weight of about 25 g were used. These animals were inoculated with a section of the neoplasm (Sa-180) and were divided into groups: the first of control - 10 mice; and two to four groups of "under treatment" ones (seven mice each).

The compounds investigated were administered intraperitoneally in appropriate doses, after previous determination of the maximum tolerance dosage.

A criterion of the evaluation the anti-neoplastic activity of the compounds tested was accepted wherein the percent difference between mean weights of the nodules (tumours) of control mice and of those which received the preparations, taking into account the toxic effects. As active compounds, those compounds were accepted which, at least in two tests, inhibited the growth of these neoplastic nodules (tumours) by more than 40%, whereas they did not cause both death of animals (less than two mice), and mean weight losses higher than 4 g.

The investigation in vivo of individual compounds of the present invention, were carried out many times, e.g., for the preparation marked with a code number C-846, that is, of 1-nitro-9-isopropylaminopropylaminoacridine dihydrochloride 24 times, and it was proved, that the inhibitions of growth of Crocker's sarcoma (Sa-180), depending on the dosage, were as follows: at doages 0.2 to 0.4 mg/kg the percent of inhibition was from 67 to 81, respectively.

For the preparation marked with a code number C-845, that is, for 1-nitro-9-ethylaminopropylaminoacridine dihydrochloride, were obtained the following inhibition values of Crocker's sarcoma (Sa-180): 48%, 49% and 57%, in a dosage of 0.2 mg/kg.

The biological activity analysis was supported by detailed pharmacologic examinations. After observations made over 72 hours, it was determined that the $LD_{50}$-value for the preparation C-846 for mice and rats (in mg/kg), was as follows:

|  | i.v. | p.o. |
| --- | --- | --- |
| mouse | 2.2 ± 0.1 | 126.2 ± 24.7 |
| rat | 0.95 ± 0.1 | 126.7 ± 17.8 |

Moreover, the maximum tolerance dosage (MTD) for mice and rats was determined (in mg/kg), as follows:

|  | i.v. | p.o. |
| --- | --- | --- |
| mouse | 1.85 | 27.21 |
| rat | 0.63 | 75.04 |

The preparation did not have any effect on the arterial blood pressure, as well as on the respiratory function of rabbits and cats after intraperitoneal administration in dosages up to 10 mg/kg. The same preparation, administered by intravenous injection in dosages of 2 mg/kg, led to an insignificant and transient hypotony, accompanied by instinctive acceleration of deepened respiration. After large dosages, more than 8 mg/kg, parallel transient changes in electrocardiograms were noted, due to the disturbances of the atrio-ventricular and intra-ventricular conductivity, namely a prolongation of the PQ segment, and a dilation of the QRS-Complex. The lethal dosages for rabbits and cats, about of 15 mg/kg (i.v.), caused a permanent hypotony and respiration disturbances or even apnoea.

In the system in vivo and in vitro the preparation showed spasmolytic activity. On a model of isolated small intestine of guinea-pig (concentration $5 \times 10^{-6}$) and of rat (concentration of $10^{-5}$), a decrease was noted in the muscular tension and an atrophy of spontaneous intestine peristalsis. In investigations in vivo, such an activity regarding the small intestine or rabbit and of cat, as well as to the muscular coat of the urinary bladder was registered after the intravenous administration (injection) of the preparation in dosages of more than 5 mg/kg.

The preparation did not demonstrate any evident and oriented activity on the central nervous system; dosages up to 1/10 $LD_{50}$ did not influence the action of hypnotic agents by mice (i.e., luminal, chloral hydrate) and of convulsant agents (Cardiazol, strychnine). It also did not influence in such dosages in essential manner the spontaneous and forced situation motor activity of mice.

Prolonged investigations were carried out on rats and rabbits during the whole three-month-exposition period of time, introducing dosages corresponding to 1/150, 1/100 and 1/50 of the $LD_{50}$-value. This last dosage was a dosage which was maximally tolerated during this period of time.

The hepatic functional tests (AlAt-Alamin aminotransferase, AspAt — Asparagine aminotransferase, both acid and alkaline phosphatases, thymol turbidity test) did not show an occurrence of any pathologic lesions. Only an insignificant (and only after the highest dosages, and with prolonged time of exposition), increase in activity of the acid phosphatase was observed. Simultaneously, some renal tests were carried out (creatinine clearance, glomerular filterability) which did not show any deviation from the norm. It also could not be proved, that the preparation had influence on either the peripheral blood (leukocytic and erythrocytic blood system, blood platelets, hematocrit, hemoglobin), or on the medular hematopoietic system. However, a certain prolongation was noted, in the third month, of the blood coagulation time.

Histologically, within the range of the lymphatic system, a decrease in the amount of the reproductive centers was noted, as well as a decrease in the amount of the small lymphocytes. Moreover, some degenerative lesions appeared in a range of the germinal epithelium, in the range of testicles, some disturbances in spermatogenesis, a decrease in the amount of sperm cells, (spermatozoa); moreover, a desquamation (desfoliation) of the intestinal epithelium and an atrophy of the glandular texture, had taken place there. Over and above this, the internal organs did not show any other microscopic changes.

The preparation did not inhibit either the capacity of rats to conceive or induce conception, or the ability of females to become pregnant; nevertheless the amount of infant animals in the brood was decreased their ontogenetic development was retarded. However, no macroscopic malformations were observed.

The preparation, in concentrations of from 0.05 to 1.0%, exerted a local irritating action. These changes caused by the intravenous injection could be eliminated by applying, as a solvent, a phosphate buffer solution at pH 7.

The advantage of the present invention, is the obtention of new compounds, which are characterized by a high anti-neoplastic activity, which has been confirmed by the above in vitro and in vivo tests.

In contrast, the group of derivatives of 1-nitro-9-dialkylaminoalkaneaminoacridine, which are known and described above, the derivatives of the present invention are characterized by an important higher stability, especially in aqueous solutions, what is a very valuable property when considering their storage. It makes possible a preparation of various medicinal forms, applied in the case of larger neoplastic spectra, than previously, as of preparation C-283 of the formula 2, where n = 2 or 3, and $R_1 = R_2$ and is a methyl or ethyl group.

The 1-nitro-9-alkylaminoalkylaminoacridines and the method for obtaining the same are illustrated by examples given below.

EXAMPLE I

To 3.4 g of (1-nitroacridyl-9)-pyridinium chloride is added 15 g of phenol, and then is heated for 15 minutes at temperature of 50° C. It is subsequently cooled, and 2.4 g of 3-isopropylaminopropylamine dihydrochloride is added and is heated anew for 45 minutes at a temperature of 80° C. The reaction mixture is cooled and 20 ml benzene is added; the whole mixture is poured into a concentrated 20% solution of potassium hydroxide. After making it alkaline, it is extracted with anhydrous benzene, (three times). The combined benzene extracts are dried with anhydrous magnesium sulphate, and after filtering off the drying agent it is acidified with an ether solution of hydrogen chloride.

The precipitated orange-colored oil is dissolved in anhydrous ethanol, then heated with activated carbon, and after filtering off the carbon, dry ether is added, and the mixture is left for crystallization. Orange-colored crystals of the 1-nitro-9-isopropylaminopropylaminoacridine dihydrochloride are obtained with a melting point of about 230° C. (with decomposition). The yield is 78%.

In a similar manner, the citrate salt is obtained with a melting point of about 300° C., the tartrate with the melting point of 150° C. as well as other salts. Chromatographic analysis is carried out on neutral alumina (Type E) using the system; benzene:ethyl acetate:ammonia (15:59:1), gave an $R_F$ equal to 0.60.

Elementary analysis for the formula: $C_{19}C_{24}N_4O_2Cl_2$: calculated: 55.79%C, 5.90%H, 13.70%N, found: 55.96%C, 5.66%H, 13.61%N.

EXAMPLE II

1-Nitro-9-chloroacridine (2.51 g) is dissolved in 10 g. of phenol and is heated for 15 minutes at a temperature of 60° C. After cooling the reaction mixture is made alkaline with a 20% aqueous solution of potassium hydroxide, and then the resulting precipitate is filtered, washed with ether and dried under vacuum.

To 3 g of the resulting 1-nitro-9-phenoxyacridine is added 1 g of N-ethylaminopropylamine, and is heated at a temperature of 90° C. for 0.5 hour. The reaction mixture is cooled, 20 ml ether is added and the whole mixture is slowly poured into an excess of ether (about 500 ml). The resulting monohydrochloride precipitate is acidified with an ether solution of hydrogen chloride, filtered off and crystallized twice from absolute ethanol.

In this manner, 2.8 g of 1-nitro-9-ethylaminopropylaminoacridine dihydrochloride is obtained with a melting point of about 255° C., (with decomposition).

Chromatographic analysis (TLC - Thin Layer Chromatography) on neutral alumina (Type E), using the system: cyclohexane: acetone; ammonia (37:37:1) gives an $R_F$ value = 0.54.

Elementary analysis for the formula: $C_{18}H_{22}O_2N_4Cl_2$ . ½ $H_2O$; calculated: 53.12%C, 5.70%H, 13.77%N, found: 53.65%C, 5.45%H, 13.73%N.

EXAMPLE III (1-Nitroacridyl-9)-pyridinium chloride (2.0 g) is heated with 10 g of phenol for 10 minutes at a temperature of 80° C. After cooling, 1.5 g of benzylaminopropylamine dihydrochloride is added, and the mixture is heated anew for 1 hour at a temperature of 100° C. After cooling, it is poured into a large amount of an aqueous solution of sodium hydroxide.

The resulting oily precipitate is extracted with ethyl acetate. Upon addition of an ether solution of hydrogen chloride, 1-nitro-9-benzylaminopropylaminoacridine dihydrochloride is precipitated, which is crystallized from a mixture of methanol and ether.

1-Nitro-9-benzylaminopropylaminoacridine dihydrochloride 1.25 g (by 50% yield) is obtained, with a melting point of 198° C.

Chromatographic analysis (TLC-Thin Layer Chromatography) on neutral alumina (Type E) using the system: cyclohexane:ethyl acetate: ammonia (37:37:1) gave an $R_F=0.37$.

Elementary analysis for the formula: $C_{23}H_{24}N_4O_2Cl_2$; calculated: 57.86%C, 5.49%H, 11.74%N, obtained: 57.72%C, 5.26%H, 11.60%N.

EXAMPLE IV (1-Nitroacridyl-9)-pyridinium chloride (2 g) and about 10 g phenol is heated for 10 minutes at a temperature of 80° C. Subsequently it is cooled, and 1.3 g of isopentylaminopropylamine dihydrochloride is added, and the mixture is then heated for 1.5 hour at a temperature of 100° C. The compound is isolated identically to that in Example III, resulting in 1.25 g (50% yield) of the 1-nitro-9-isopentylaminopropylaminoacridine dihydrochloride with a melting point of 180° C. (with decomposition).

Chromatographic analysis on neutral alumina (Type E) using the system: cyclohexane:ethyl acetate:ammonia (37:37:1) gave an $R_F = 0.50$.

Elementary analysis for the formula:

$C_{21}H_{28}N_4O_2Cl_2 \cdot H_2O$ calculated: 55.15%C, 6.61%H, 12.25%N.
obtained: 55.53%C, 6.67%H, 12.23%N.

EXAMPLE V (1-Nitroacridyl-9)-pyridinium chloride (3.4 g) and 15 g of phenol is heated for 10 minutes at a temperature of 80° C. After cooling, 1.16 g of propylaminopropylamine is added and heated for 1.5 hours at a temperature of 100° C. It is then treated as in Example III, obtaining at least 1.8 g of 1-nitro-9-propylaminopropylaminoacridine dihydrochloride with a melting point of 234° C. (with decomposition).

Chromatographic analysis of neutral alumina (Type E) using the system: benzene:methanol (10:1) gave an $R_F = 0.4$.

Elementary analysis for the formula: $C_{19}H_{24}N_4O_2Cl_2$ calculated: 55.47%C, 5.88%H, 13.62%N, obtained: 55.48%C, 5.87%H, 13.51%N.

EXAMPLE VI 3.4 g (0.01 of mole) of a pyridinium-derivative of 1-nitroacridine and about 15 g of phenol is heated for 15 minutes at a temperature of 80° C. Is is then cooled, and 1.6 g of 3-methylaminopropylamine dihydrochloride is added and heated for 0.5 hour at a temperature of 80° C.

It is then isolated analogously as in Example I, obtaining 1-nitro-9(-3-methylaminopropylamino)acridine dihydrochloride, dark yellow crystal, and having a melting point of about 255° C. (with decomposition).

Chromatographic analysis on neutral alumina (Type E) using the system: n-heptane:acetone:ammonia (35:35:1) gave an $R_F$ value = 0.27.

Elementary analysis for the formula: $C_{17}H_{20}N_4O_2Cl_2$. calculated: 52.68%C, 5.29%H, 14.38%N, obtained: 52.35%C, 5.35%H, 14.63%N.

EXAMPLE VII (1-Nitroacridyl-9)-pyridinium chloride (3.4 g) is dissolved in 10 g phenol and is heated for 15 minutes at a temperature of 80° C. After cooling, 2.1 g of 3-butylaminopropylamine hydrochloride is added and is heated anew for one hour at a temperature of 80° C. It is cooled and ether is added; the whole mixture is poured into a cooled aqueous solution of sodium hydroxide. It is extracted with ether, the ether extracts are dried, and it is then acidified with an ether solution of hydrogen chloride.

The hygroscopic precipitate formed is crystallized many times from a mixture of absolute ethanol and ether. 1-Nitro-9-butylaminopropylaminoacridine dihydrochloride is obtained with a yield of 82%, and a melting point of 215° C. (with decomposition).

Thin Layer Chromatography on neutral alumina (Type E) using the system: benzene:ehtyl acetate; ammonia (15:59:1) gave an $R_F = 0.86$.

Elementary analysis for the formula: $C_{20}H_{26}N_4O_2Cl_2$ calculated: 55.60%C, 5.94%H, 12.97%N found: 55.43%C, 5.98%H, 12.70%N.

EXAMPLE VIII (1-Nitroacridyl-9)-pyridinium chloride (1.7 g) and 10 g phenol is heated for 10 minutes at a temperature of 80° C. After cooling, the reaction mixture is dissolved in ether and is poured slowly into a cooled solution of potassium hydroxide. It is then extracted many times with ether. The etheric extract prior to drying, is distilled off to a half of its volume, cooled and filtered, to obtain the 1-nitro-9-phenoxyacridine precipitate. 1.5 g of cyclohexylaminopropylamine hydrochloride were added and heated at 100° C. for 2 hours. After cooling, the reaction mixture was dissolved in ether and slowly poured into cold solution of KOH and then extracted with ether. The ether extracts were pooled, dried, and evaporated to ⅓ volume. The yellow precipitate of 1-nitro-9-cyclohexylaminopropylaminoacridine (free base) were recrystallized from a mixture of benzene and ether, m.p. 150° C. (with decomposition).

Chromatographic analysis (TLC-Thin Layer Chromatography) on neutral alumina (Type E) using the system: benzene:methanol (10:1) gave an $R_F = 0.3$.

Elementary analysis for the formula: $C_{22}H_{23}N_4O_2Cl_2 \cdot H_2O$; calculated: 56.29%C, 6.44%H, 11.94%N, found: 56.15%C, 6.33%H, 11.70%N.

EXAMPLE IX

1-Nitro-9-phenoxyacridine (3.16 g), 10 g of phenol and 1.6 g of ethylaminoethyleneamine hydrochloride are heated for 45 minutes at a temperature of 80° C. Then it is treated similarly, as in Example VII.

An orange-colored precipitate of 1-nitro-9-ethylaminoethylaminoacridine dihydrochloride is obtained with a melting point of 238° C. (with decomposition).

Chromatographic analysis (TLC-Thin Layer Chromatography) on neutral alumina (Type E) using the system: benzene:ethyl acetate:ammonia (15:59:1) gave an $R_F = 0.6$.

Elementary analysis for the formula: $C_{19}H_{24}N_4O_2Cl_2$; calculated: 55.52%C, 5.89%H, 13.63%N; found: 55.53%C, 5.94%H, 13.39%N.

EXAMPLE X

1-Nitro-9-phenoxyacridine (1.6 g), 0.8 g of butylaminoethyleneamine dihydrochloride and 7 g of phenol are heated at a temperature of 100° C. for 1.5 hour. The condensation product is isolated from the reaction medium in a similar manner as in Example VII.

There is obtained 1.4 g (70% yield) of 1-nitro-9-butylaminoethylaminoacridine dihydrochloride with a melting point of about 227° C.

Chromatographic analysis on neutral alumina (Type E) using the system: cyclohexane:ethyl acetate:ammonia (37:37:1) gave an $R_F = 0.55$.

Elementary analysis for the formula: $C_{19}H_{24}N_4O_2Cl_2$; calculated: 55.52%c, 5.89%H, 13.63%N.; obtained: 55.59%C, 5.94%H, 13.39%N.

EXAMPLE XI 3.4 g (equal to 0.01 mole) of (1-nitroacridyl-9-pyridinium)chloride is heated with 15 g of phenol for 15 minutes at a temperature of 60° C. It is then cooled, and 1.5 g of methylaminoethylamine dihydrochloride is added, and it is again heated to a temperature of 80° C. for 0.5 hour. Then it is cooled and made alkaline with a 10% solution of sodium hydroxide. The orange-colored precipitate of 1-nitro-9-methylaminoethylaminoacridine monohydrochloride is dried, and is then suspended in a small amount of ether, owing to its complete insolubility either in ether, or in benzene, and it is acidified with a solution of hydrogen chloride. After crystallization from dry methanol, 1-nitro-9-methylaminoethylaminoacridine dihydrochloride is obtained with a yield of 65%, melting point 255° C. (with decomposition).

Chromatographic analysis (TLC-Thin Layer Chromatography) on neutral alumina (Type E) using the system: benzene:acetone:ammonia (3:1:2) — was precipitated, and after separation of the layers, to the higher layer methanol was in quantitative ratio (1:10). The $R_F = 0.46$.

Elementary analysis for the formula: $C_{16}H_{18}N_4O_2Cl_2$; calculated: 52.65%C, 4.97%H, 15.35%N, obtained: 52.49%C, 5.01%H, 15.35%N.

EXAMPLE XII (1-Nitroacridyl-9)-pyridinium chloride (1.7 g) and 10 g of phenol are heated for 15 minutes at temperature of 80° C. After cooling, 1.1 g of cyclohexylaminoethylamine dihydrochloride is added and is heated anew at a temperature of 120° C. for 2 hours.

The condensation product is isolated in a similar manner as in the Example XI. There is obtained 2.4 g (yield of 55%) of 1-nitro-9-cyclohexylaminoethylaminoacridine dihydrochloride with a melting point of about of 280° C. (with decomposition).

Chromatographic analysis on neutral alumina (Type E) using the system: cyclohexane:ethyl acetate:ammonia (37:37:1) giving an $R_F = 0.37$.

Elementary analysis for the formula: $C_{21}H_{27}N_4O_2Cl_2$; calculated: 57.58%C, 6.21%H, 12.79%N; obtained: 57.71%C, 6.23%H, 12.82%N.

EXAMPLE XIII

1-Nitro-9-phenoxyacridine (3.16 g), 15 g of phenol and 1.75 g of isopropylaminoethylamine dihydrochloride are heated at a temperature of 90° C. for one hour.

The condensation product is isolated in a similar manner as in Example VII. There is obtained 2.38 g (yield, 60%) of 1-nitro-9-isopropylaminoethylaminoacridine dihydrochloride with a melting point of 235° C. (with decomposition).

Chromatographic analysis on neutral alumina (Type E) using the system: ethyl acetate:ethanol (10:1) gave an $R_F = 0.9$.

Elementary analysis for the formula: $C_{18}H_{22}N_4O_2Cl_2 \cdot H_2O$; calculated: 52.09%C, 5.34%H, 13.50%N; obtained: 52.00%C, 5.40%H, 13.43%N.

EXAMPLE XIV

1-Nitro-9-phenoxyacridine (1.58 g) is dissolved in about 5 g of phenol, and then 0.95 g of 2-isobutylaminoethylamine dihydrochloride is added and is heated at a temperature of 90° C. for 1.2 hour. It is isolated in a similar manner, as in Example VII. There is obtained 1-nitro-9-isobutylaminoethylaminoacridine dihydrochloride with a melting point of 230° C. (with decomposition).

Chromatographic analysis on neutral alumina using the system: cyclohexane:ethyl acetate;ammonia (37:37:1) gave an $R_F = 0.4$.

Elementary analysis for the formula: $C_{20}H_{26}N_4O_2Cl_2$; calculated: 56.78%C, 5.72%H, 13.25%N; obtained: 56.63%C, 5.68%H, 13.15%N.

EXAMPLE XV

1-Nitro-9-phenoxyacridine (3.16 g) is dissolved in 15 g of phenol, and 1.2 g N-propylethylenediamine is added; then it is heated for 1.0 hour at a temperature of 80° C.

The condensation product is isolated in a similar manner, as in Example XI. There is obtained 1.2 g of 1-nitro-9-propylaminoethylaminoacridine dihydrochloride with a melting point of 260° C. (with decomposition).

Chromatographic analysis on neutral alumina using the system: benzene:methanol (10:1) gave an $R_F = 0.9$.

Elementary analysis for the formula: $C_{18}H_{22}N_4O_2Cl_2$; calculated: 54.45%C, 5.59%H, 14.11%N; obtained: 54.59%C, 5.40%H, 14.13%N.

We claim:

1. A compound selected from the group consisting of a 1-nitro-9-alkylaminoalkylaminoacridine of the formula 1,

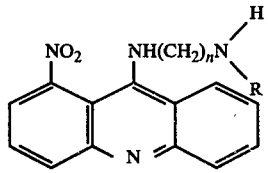

wherein R is selected from the group consisting of methyl, ethyl, propyl, isopropyl, butyl, isobutyl, isopentyl, benzyl and cyclohexyl, wherein n is equal to 2 or 3 and salts thereof.

* * * * *